(12) United States Patent
Porter et al.

(10) Patent No.: US 6,634,393 B2
(45) Date of Patent: Oct. 21, 2003

(54) SIPHONING DEVICE FOR USE IN BASTING, MEASURING OR IMMISCIBLE LIQUID SEPARATION

(76) Inventors: Jerry Porter, 2818 Jutland Rd., Kensington, MD (US) 20895; Edward Poslinski, 5573 Donnelly Cir., Orlando, FL (US) 32821; Stephen Graner, 5504 Pine Shade Ct., Orlando, FL (US) 32819

( * ) Notice: Subject to any disclaimer, the term of this patent is extended or adjusted under 35 U.S.C. 154(b) by 0 days.

(21) Appl. No.: 09/930,809

(22) Filed: Aug. 16, 2001

(65) Prior Publication Data

US 2002/0020463 A1 Feb. 21, 2002

Related U.S. Application Data

(60) Provisional application No. 60/225,575, filed on Aug. 16, 2000.

(51) Int. Cl.$^7$ ................................................ B67C 3/00
(52) U.S. Cl. ........................... 141/8; 141/26; 141/352; 141/357
(58) Field of Search ............................. 141/21–29, 310, 141/335, 351–357, 4–8; 99/345, 346

(56) References Cited

U.S. PATENT DOCUMENTS 1,977,062 A * 10/1934 Higley .................... 141/26
5,638,872 A    6/1997 Porter
5,875,823 A    3/1999 Porter

* cited by examiner

Primary Examiner—Timothy L. Maust
(74) Attorney, Agent, or Firm—Sheldon H. Parker

(57) ABSTRACT

An improved siphoning device having an elongated hollow body member having a first open tip end with a fluid flow opening and a second open end. A two-way liquid valve is positioned within the first open tip end, and air pump member is removably attached to the second end of the body member. The seal member is movably positioned within the first open tip end. An air vent exhausts hot gases and is an air outlet for pumping air out of the body and creating suction within body. The air vent is preferably positioned proximate the elongated body second open end and has a cross-sectional area substantially less than the fluid flow opening cross-sectional area. The air vent preferably has a diameter in the range from at least one thirty second of an inch to three thirty seconds of and inch. Most preferably the diameter is greater than one thirty second is of an inch and less than three thirty seconds of and inch. Most preferably the diameter is about two thirty seconds of an inch. A vent collar is provided for directing any fluid flow out of the air vent, down and away from the user, to protect the user from the hot gases that can be exhausted through the air vent and any inadvertent exiting of liquid.

32 Claims, 6 Drawing Sheets

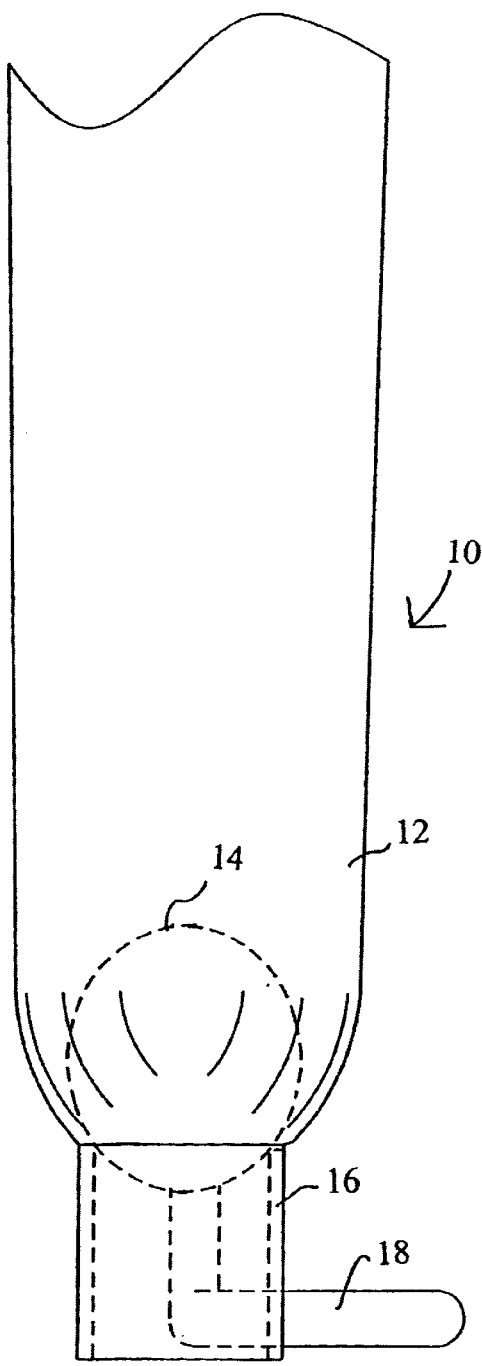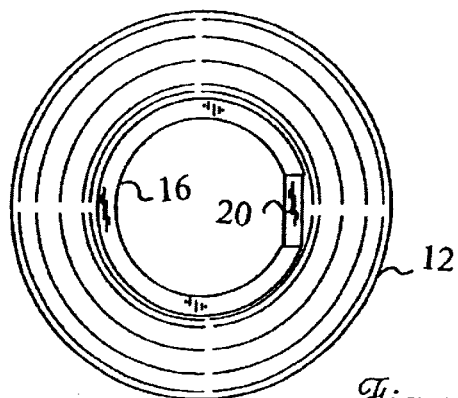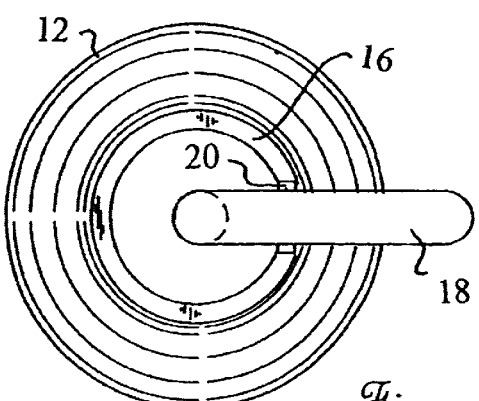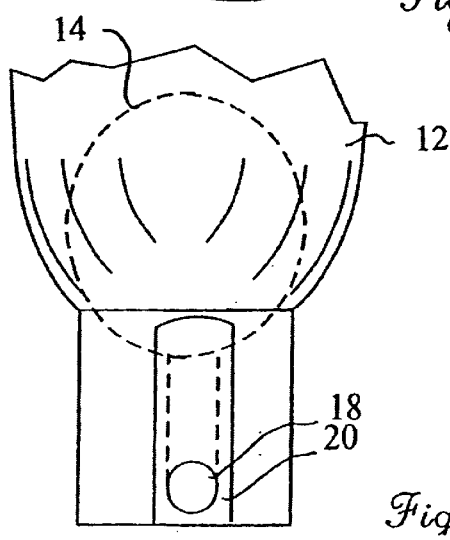
Figure 1
Figure 2
Figure 3
Figure 4

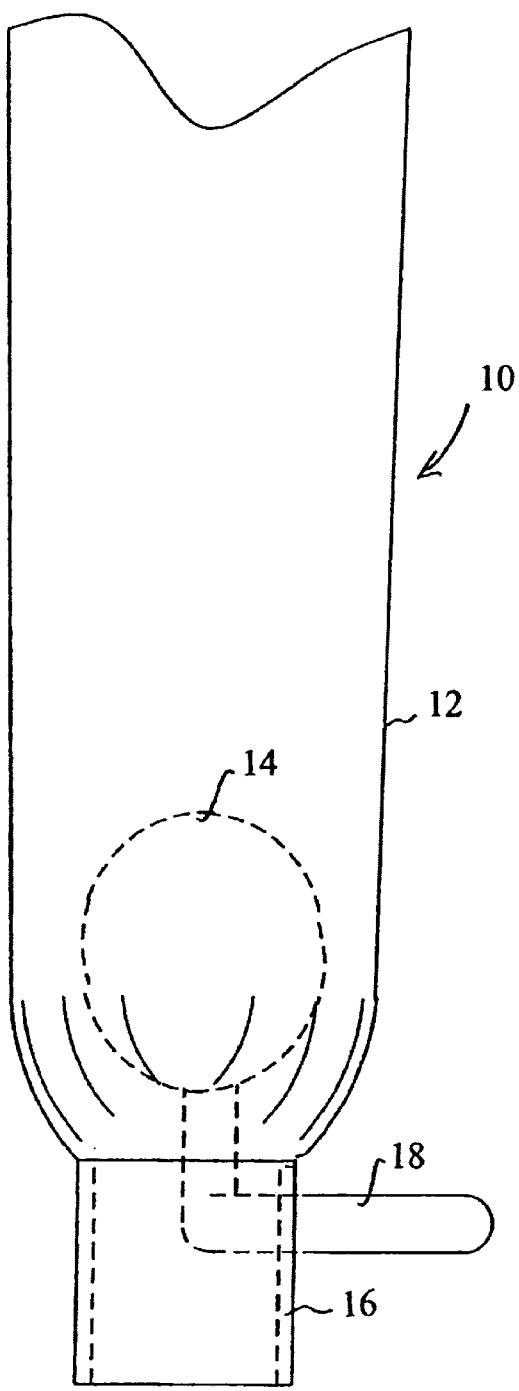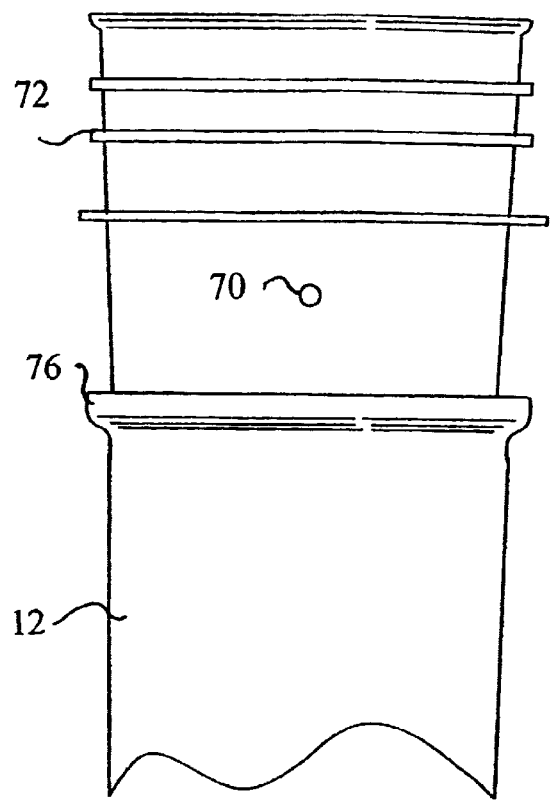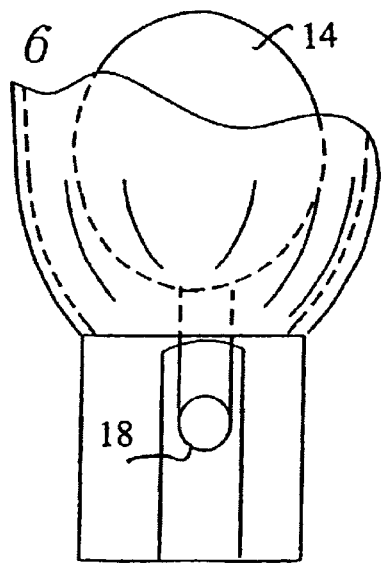

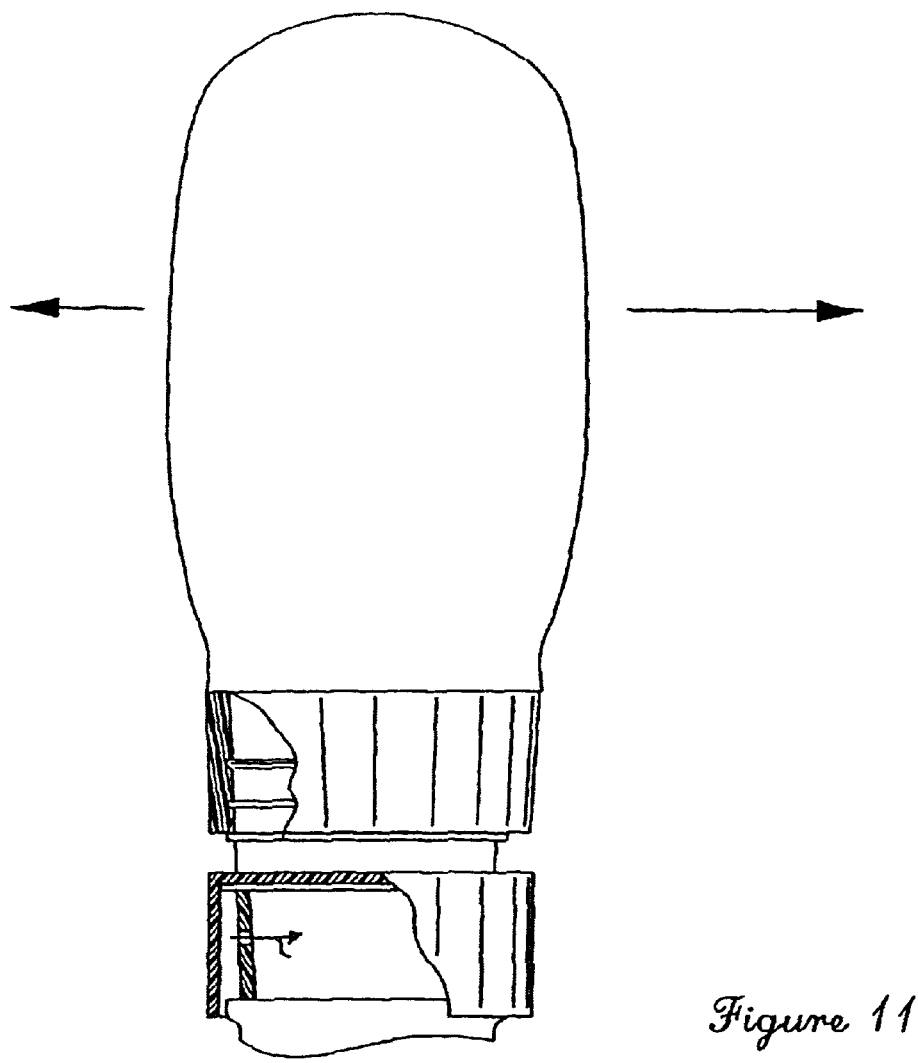
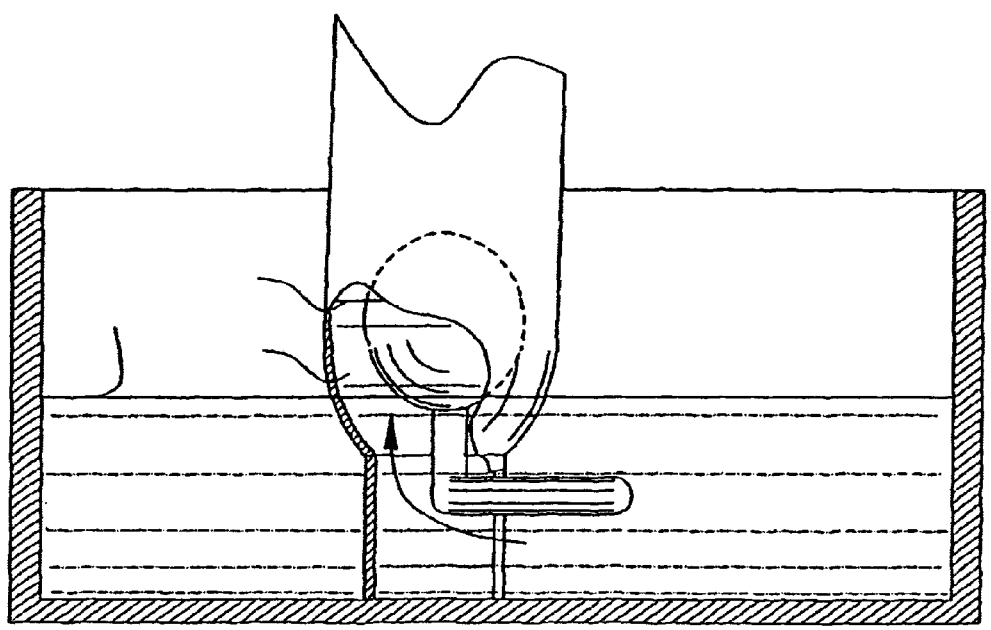
Figure 11

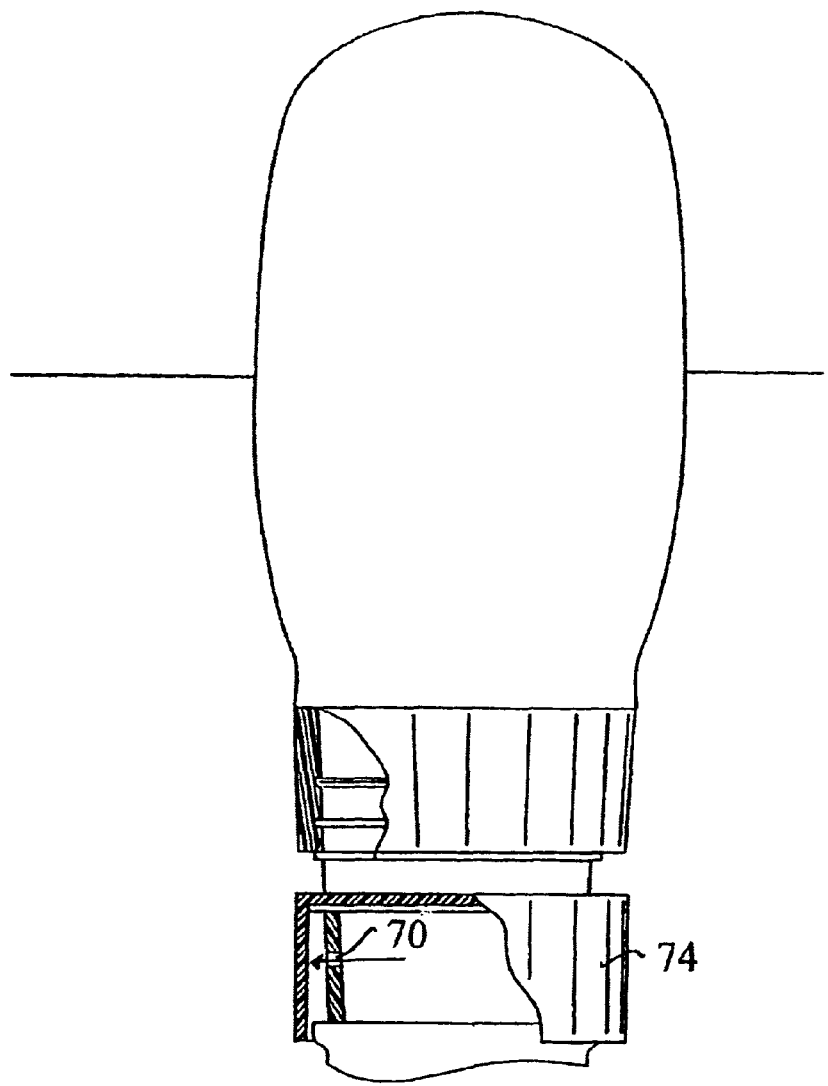
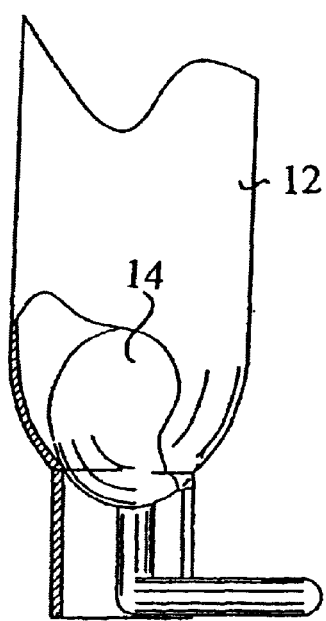
Figure 12

SIPHONING DEVICE FOR USE IN BASTING, MEASURING OR IMMISCIBLE LIQUID SEPARATION

This application claims the benefit of Provisional Application No. 60/225,575, filed Aug. 16, 2000.

BACKGROUND OF THE INVENTION

1. Field of the Invention

The invention relates to a siphoning device having particular utility as a food baster, of the type commonly know as a turkey baster. The invention is also applicable to medical, scientific and industrial applications and can be used for the separation of immiscible liquids.

2. Brief Description of the Prior Art

The prior art devices commonly known as basters do not effectively contain the liquid that has been drawn into the device. Typically, these devices expel some of whatever liquid the user is attempting to move before the device has reached the final destination. The solution to this has been to tip the baster, directing the liquid to the bulb. This, however, increases the possibility of spillage and places the generally hot contents adjacent the user's hand.

The term baste is used in the application consistent with the definition in the American Heritage Dictionary, Third Edition, Copyright 1994, InfoSoft International, as follows: baste tr.v. basted, basting, bastes. To moisten (meat, for example) periodically with a liquid, such as melted butter or a sauce, especially while cooking baster n.

In its simplest form (hereinafter referred to as the 'simple baster') the simple baster consists of only two parts. The first part is the bulb, which is typically made of rubber or a rubber-like plastic. The bulb is generally thick and soft to allow for flexibility as the device is operated by squeezing and releasing the bulb by hand. The second part is a hollow round tube or cylinder, tapered at one end to a small opening. The bulb is attached to the tube at the wider end, with the small opening being used to collect and disperse liquids. While baking meat, to add flavoring and prevent dehydration, it is desirable to take broth or meat juices to baste the meat. The baster is employed in this endeavor by holding the device in one hand and ejecting some of the air from the bulb. The lower end of the tube is placed below the liquid surface, the bulb is released and the vacuum draws the liquid into the tube. The tube is then moved to the top of the meat being cooked, the bulb is squeezed and the liquid is ejected over the meat. In the simple baster, when the liquid is drawn into the tube, it is frequently hot. The hot liquid heats the air in the tube and the bulb, causing expansion of the air. The expansion of the air forces at least some of the liquid out the tube. It is often impossible to draw or retain enough liquid in the baster to adequately baste the meat. Attempts to contain the liquid by turning the tube over, bulb end down, can leak hot liquid in an uncontrollable and dangerous fashion. Turning the baster all the way places the bulb, filled with hot liquid, near the user's hand and may cause burns through the flexible bulb.

The simple baster is often used to separate the meat juices into their component lighter fat and heavier water-soluble parts. When separated from the fat, the heavier water-soluble material is frequently used as a component in gravies. The heavier materials will be referred to as 'flavorings'. While it would be desirable to wait for a brief time for the fat and flavorings to separate, for distribution into different containers, this is not always feasible. The nature of the simple baster is not well suited for use as a separator because the contents begin to exit as soon as they have entered, often with outside air bubbling through and remixing the liquids to be separated. Any attempts to draw all the pan juices into the baster for separating in one operation results in mixing the pan juices, just the opposite of the desired separation.

Another shortcoming of the simple baster is the inability to measure or control the exact amount of liquid delivered by the baster. The only control over the volume entering the tube occurs when the bulb is squeezed a particular amount or the inlet pulled out of the liquid. The user must estimate how much to squeeze the bulb prior to insertion into the liquid, since squeezing the bulb after the tube has been partially filled drives the liquid out of the baster. Thus, the device cannot be operated in a cumulative manner.

The simple baster, or a similar device, can also be used for a multitude of tasks that involve moving liquids. These liquids can be hot or cold, acid or base, aqueous or not, highly fluid or partially viscous.

In summary, the prior art simple basters are deficient in at least four ways:
1. Fluid leaks due to flow under the force of gravity.
2. When hot liquid is used, air above the liquid expands and pushes the liquid out, making the handling of liquids difficult and dangerous.
3. The amount of liquid that can be drawn up is limited by the size of the bulb and the air trapped within the bulb.
4. Making exact liquid measurements are difficult, because of leaking of the device and the inability to control the amount of liquid drawn into the device.

Prior U.S. Pat. Nos. 5,875,823 and 5,638,872 to Porter disclose and claim devices that overcome prior art problems. It is an object of the present invention to provide an improved design that is less costly to manufacture and easier to use.

SUMMARY OF THE INVENTION

The invention relates to an improved siphoning device, particularly of the type used for basting foods. The device includes an elongated hollow body member having a first open tip end with a fluid flow opening and a second open end. A two-way liquid valve is positioned within said first open tip end, and air pump member is removably attached to the second end of the body member. The air pump is used to expel air from the hollow body member and to draw or siphon liquid into the hollow body member.

The two-way liquid valve has an elongated stem member and a seal member. The seal member is movably positioned within the first open tip end, and is movable between a first position and a second position. The seal member engages the interior surface of the body member proximate the first open tip when in the first position, thereby precluding fluid flow out of the hollow body member first open tip end. It disengages the interior surface of the outlet region when in the second position, thereby permitting flow into or out of the hollow body member.

The stem member has a first end and a second end, with the second end affixed to the seal member to enable the stem to travel with the seal member. The stem member's first end extends substantially beyond the open tip end exterior of the body, so that when the seal member is in the first position, the stem's first end extends through and substantially beyond the open tip end. When the stem's first end is moved toward the open tip end, the seal member is moved away from the interior surface of the outlet region, enabling fluid flow.

The stem has an engagement member extending away from the stem at least at an acute angle, preferably forming an "L". Pressure on the engagement member in the direction of the seal member moves the seal member out of contact with the interior wall, thereby placing the liquid valve in an open position and permitting liquid to be discharged axially from the hollow body member, through the first open tip end fluid flow opening and along the stem member.

Preferably, the air pump member is a flexible bulb releasably affixed to the second open end of the hollow body member.

Preferably, the seal member is a ball valve member having a horizontal cross-section corresponding to the first open tip end circular cross-section. Advantageously, the ball valve member has a diameter greater than the diameter of the first open tip end and has an oval vertical cross-section.

A stem shroud extends from the first open tip end, such that its proximal end is affixed to, or an extension of the tip end, and its distal end extends beyond that of the stem when the valve member is in the closed position. Thus, when the stem shroud is positioned flush against a flat surface, the stem does not contact the flat surface and the valve is closed. The engagement member is positioned and dimensioned to extend through an elongated opening in the shroud and substantially beyond the shroud. Essentially, the shroud member has a "C" shaped cross-section.

An air vent is provided for exhausting hot gases and as an air outlet for pumping air out of the body member and creating suction within the hollow body member. The air vent is preferably positioned proximate the elongated body second open end and has a cross-sectional area substantially less than the fluid flow opening cross-sectional area. In this manner, it functions as a one way valve by substantially restricting air flow into said body relative to fluid flow through the fluid flow opening.

The air vent preferably has a diameter in the range from at least one thirty second of an inch to three thirty seconds of and inch. Most preferably, the diameter is greater than one thirty second of an inch and less than three thirty seconds of and inch. Most preferably, the diameter is about two thirty seconds of an inch. By way of contrast, the fluid flow-opening diameter is about one quarter of an inch, and would have a range comparable to that of the air vent. The ratio of the air vent cross-sectional area to the fluid flow opening cross-sectional area must be low enough to assure that the siphoning action draws in a minimal amount of air, that is, the fluid intake is predominantly liquid entering through the fluid flow opening. A fluid flow opening has a cross-sectional area on the order of at least about 100 mm.

A vent collar is advantageously provided for directing any fluid flow out of the air vent, down and away from the user. In this manner, the user is protected from the hot gases that can be exhausted through the air vent and any inadvertent exiting of liquid, as for example, due to overfilling of the hollow body member. The vent collar is supported on the hollow body member over and spaced from the air vent, such that airflow into the body member, through the air vent, is not closed by the collar member.

A radially outward extending flange member is provided on the hollow body. The flange member is positioned between the air vent and the elongated body second open end. The vent collar has a radially inward extending flange region, dimensioned and positioned such that the vent collar flange region is supported on the hollow body flange member.

The vent collar has is cylindrical in shape, corresponding to the cylindrical shape of the body member, and has a first end proximal to the hollow body second open end and a second end distal relative to the hollow body second open end. The collar's flange region extends from the hollow body member's proximal end. The vent collar distal end having a radius at least about 1 mm and preferably about 2 mm greater than the radius of the elongated body member, to provide an air flow clearance.

The method of liquid transfer using the above described device includes the steps of: pumping air out of the air vent hole by constricting the air pump member; inserting the outlet region into a liquid, before or after the previous step, such that the outlet of the outlet region is below the surface of the liquid; siphoning liquid into the device, by releasing the air pump member. Once the air pump member is released, air is substantially prevented from entering the hollow body member due to the air vent's relatively small cross-sectional area. The device is withdrawn from the outlet region from the liquid, while the two-way liquid valve restricts flow of liquid out of the device. The device is moved to a desired location. The liquid valve is activated to allow the liquid to flow from the body member to the desired location, thus dispensing at least a portion of the liquid at the desired location. The air pump is repeatedly activated while the outlet of the outlet region is below the surface of said liquid, thereby repeatedly drawing liquid into the device. During this step the vent collar protects a user from inadvertent contact with liquid that flows out of the air vent hole, and the liquid valve prevents the flow of liquid from the device while permitting fluid flow into the device.

During the operation of the device, air is expelled via the air vent hole through the step of compressing the air pump member. However, the relative dimensions of the air vent, the body member and the liquid outlet, restrict the airflow into the body member via the air vent, thus enabling the air vent to function as a one-way valve with no moving parts.

The dimension relation is critical to provide siphoning predominantly of liquid into the device and while only a relatively small amount or minimal amount of air flows into the device via the air vent hole.

BRIEF DESCRIPTION OF THE DRAWINGS

The advantages of the instant disclosure will become more apparent when read with the specification and the drawings, wherein:

FIG. 1 is a cutaway side view of the baster in liquid retaining position;

FIG. 2 is a cutaway front view of the dispensing tip in the position of FIG. 1;

FIG. 3 is a cutaway end view of the dispensing tip and L-shaped valve;

FIG. 4 is a cutaway end view of the dispensing tip without the L-shaped valve;

FIG. 5 is a cutaway side view of the baster in liquid dispensing position;

FIG. 6 is a cutaway front view of the dispensing tip in the position of FIG. 5;

FIG. 7 is a cutaway front view of the air vent of the disclosed invention;

FIG. 11 is a cutaway side view of the baster gathering liquid; and

FIG. 12 is a cutaway side view of the baster evacuating air.

DETAILED DESCRIPTION OF THE PREFERRED EMBODIMENTS OF THE INVENTION

Figure 8:
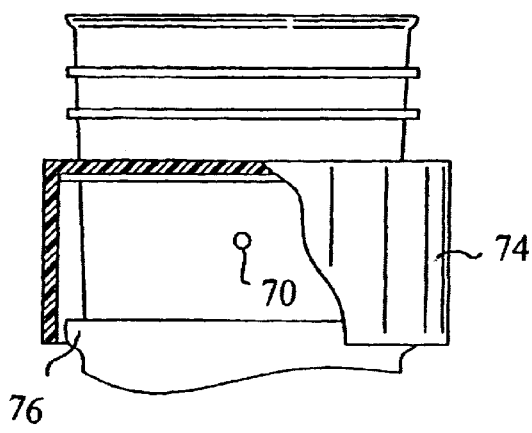
FIG. 8 is a cutaway view of the air vent of the disclosed invention with the protection ring.

U.S. Pat. Nos. 5,638,872 and 5,875,823 to Jerry Porter, which are incorporated herein as though recited in full, overcome the prior art problems by using dual valves to expel air and prevent liquids from being released until the valve is activated. The disclosed embodiments of the present invention provide improvements over the embodiments disclosed in the patents.

As is seen in the baster 10 illustrated in FIG. 1, the retaining tube 12 contains a ball valve 14 that serves to prevent the liquid within the retaining tube 12 from being released through the dispensing tip 16. While a ball valve is shown and referred to herein, the type of valve employed is not narrowly critical, and other types of valves could be used, as will be apparent to those skilled in the art. It is critical that the inlet 100 to the dispensing tip 16 be dimensioned to have a diameter less than the diameter of the ball valve 14 to permit the ball valve 14 to rest on the inlet 100 without being a recessed. This enables the ball valve 14 to move freely within the tube 12 and to move rapidly away from the inlet 100, as described further herein. Within the dispensing tip 16, and connected to the ball valve 14, is the L-shaped valve tip 18. The valve tip 18 is free to move within the dispensing tip 16 along the notch 20, illustrated in FIG. 2. Although the notch 20 can provide some horizontal movement of the dispensing tip 16, it is preferable that this movement is extremely limited to prevent accidental release of hot liquids. Additionally, the L-shape precludes the stem and valve from moving into the body of the retaining tube either in use, or during cleaning of the baster.

In the bottom view of FIG. 3, the relationship between the dispensing tip 16, the notch 20 and valve tip 18 is illustrated. In FIG. 4, the valve tip 18 is not shown in order to more clearly illustrate the notch 20 within the dispensing tip 16.

Figure 10:
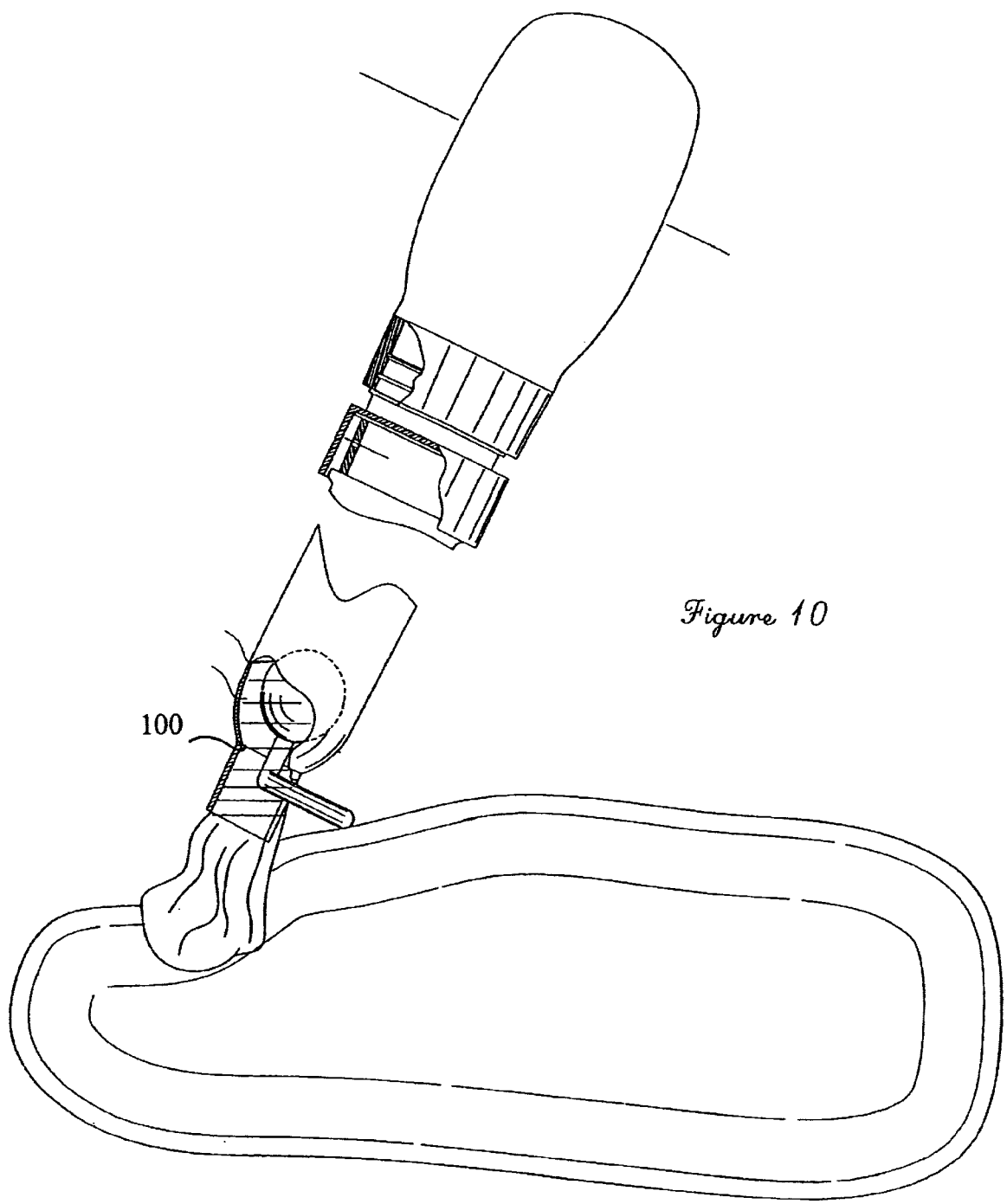
FIG. 10 is a cutaway side view of the baster dispensing liquid.

When the ball valve 14 is in the lowered position, as illustrated in FIG. 1, the liquid within the retaining tube 12 is prevented from leaving. In this position, the valve tip 18 is proximate the edge of the dispensing tip 16 and the ball valve 14 is resting on the entrance to the dispensing tip 16, blocking fluid flow. To remove the liquid from the retaining tube 12, the valve tip 18 is pressed against the object to receive the liquid, as illustrated in FIG. 10, thereby raising the ball valve 14 to the position illustrated in FIGS. 5 and 6. The vertical movement of the valve tip 18 and therefore ball valve 14, removes the valve 14 from the entrance to the dispensing tip 16, enabling liquid to flow out of the retaining tube 12.

To enable liquid to flow into the retaining tube 12, air must be dispelled from the device, to create a suction effect. To accomplish this the air pump, typically a bulb 80, on the baster 10 is squeezed, as illustrated in FIG. 12, expelling a portion of the air through the air vent 70. As the bulb 80 is released, the air within the retaining tube 12 is drawn into the bulb 80, as illustrated in FIG. 11, and the liquid is drawn into the retaining tube 12.

Venting the air from the retaining tube 12 prior to submersion in liquid can easily be done through the inlet 100 and dispensing tube 16. However, once the retaining tube 12 contains liquid, the venting can no longer be accomplished using this method. To enable air to vent the retaining tube 12 when the bulb 80 is squeezed a vent hole 70 is provided proximate the top portion of the retaining tube 12.

Figure 9:
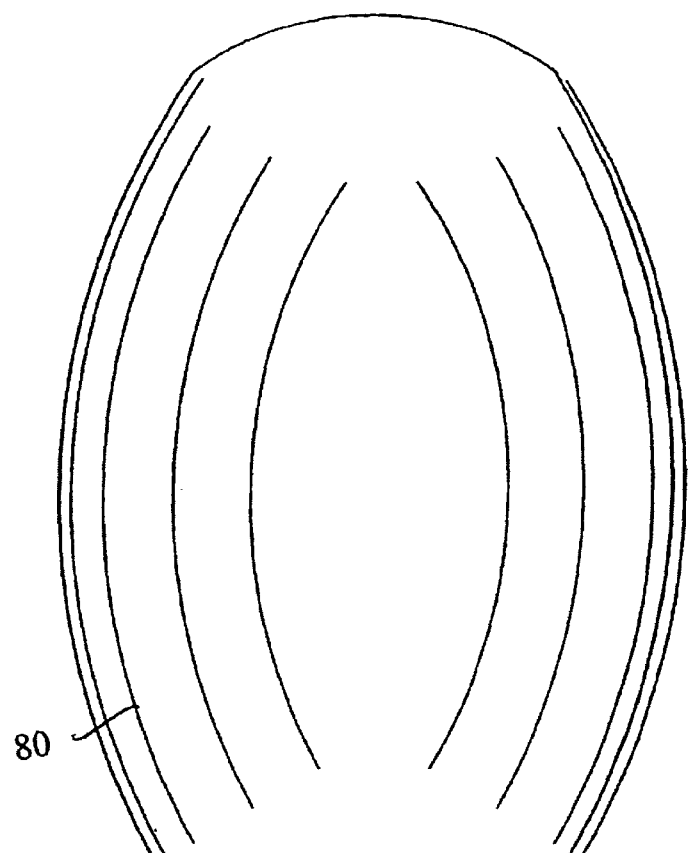
FIG. 9 is a cutaway view of the disclosed baster with the air bulb in position.

As disclosed in U.S. Pat. No. 5,638,872, FIG. 8, the vent hole can be provided with an elastic band overlying the vent hole to provide for a one way flow. It has now been found, as illustrated in FIGS. 7, 8 and 9, that the one way flow can be effectively achieved through the dimensioning of the vent hole 70 to provide for the requisite out flow and restricted in flow. The dimensioning of the vent hole 70 is, however, critical. If the diameter of the vent hole 70 is too small, the air is restrained from leaving the tube 12, thereby preventing additional liquid from being drawn into the retaining tube 12. If, however the vent hole 70 has too great a diameter, when the bulb 80 is released, more air than liquid will flow into the retaining tube 12. It has been found that a hole diameter of approximately 1.3 mm (about 0.05 inch) provides the requisite balance between permitting exit air flow and restricting entrance air flow. The size of the air vent is relative to the area of the tube 12 inlet 100, to the viscosity of the fluid and the volume of air that is being drawn through the hole due to a single pumping action. Where the air vent 70 is about 1.3 mm and the inlet opening is about 6 mm (about one quarter of an inch) or greater, the liquid is siphoned into the tube 12, in preference to air being drawn into the bulb 80, through the vent hole 70. Where the area of the liquid inlet is about 100 mm. and the tube 12 has a volume sufficient to hold about two oz. of liquid, the hole is advantageously at least 1/32 of an inch in diameter but no greater than 3/32 of an inch. Preferably the hole is greater than 2/32 and less than 3/32 of an inch. For very high viscosity liquids, the hole size will be less than for a liquid such as water or a thin gravy. The dimensions are relative and the proportional increase or decrease of the dimensions does not adversely affect the siphoning action.

The design of the bottom valve 14 must be such that it moves rapidly within the tube 12. A slow acting valve will permit air to be drawn through the vent hole 70, in preference to the liquid being drawn through the inlet 100 opening. In the disclosed device, as the valve tip 18 is pressed against a surface, the bottom inlet 100 is rapidly opened. It is critical that the valve 14 be dimensioned to freely move within the tube 12 to enable the rapid opening of the inlet 100. As illustrated in FIG. 11, when the bottom most edge 1140 of the device is resting on the bottom of the vessel, then the valve 14 opens due to the suction action resulting from the squeezing and releasing of the bulb 80, requiring that the valve 14 opens rapidly. A valve that is in the form of a bulb having an oval vertical cross-section and a circular horizontal cross-section is preferred, as illustrated in FIGS. 1, 2 and 11. In summary, the relative dimension and configurations of the vent hole 70, the bottom inlet 100 and the valve 14, must provide for substantially greater fluid flow through the bottom inlet 100 than through the vent hole 70, such that the required liquid is drawn into the tube 12 during the siphoning action. Essentially, during the siphoning step, fluid drawn in to the device by the vacuum created by the release of the compressed bulb 80 must be predominantly liquid entering through the bottom inlet 100.

The vent hole 70 is located below the bulb 80 receiving ridges 72 and covered by a ring 74, shown in FIGS. 8 and 9. The ring or collar 74 protects the vent hole 70 from food and dirt accumulation and is a shield that protects the user if the tube 12 is overfilled. Thus, if the user fills the tube 12 above the recommended fill line, without the ring 74, liquid will spray out through the air vent 70. The maximum fill line is a point substantially below the vent hole 70, and is preferably noted by a mark on the tube 12. However, if the user does inadvertently overfill the tube 12, the loose fitting ring 74 thus acts as a spray shield. The ring 74 is prevented from sliding off the baster 10 by the flange 76. The air vent also serves as an exhaust valve for the release of hot gases that accumulate in the upper region of the tube and in the bulb 80, during the siphoning process.

Since other modifications and changes varied to fit particular operating requirements and environments will be apparent to those skilled in the art, the invention is not considered limited to the examples chosen for the purposes of disclosure, and covers all changes and modifications which do not constitute departures from the true spirit and scope of this invention.

What is claimed is:

1. A siphoning device, comprising:
   an elongated hollow body member, said body member having an interior surface and a first open tip end with a fluid flow opening, said fluid flow opening having a cross-sectional dimension, and a second open end,
   a two-way liquid valve, said two-way liquid valve being positioned within said first open tip end, and
   an air pump member, said air pump member interacting with said second end of said body region to expel air from said hollow body member and to draw liquid into said hollow body member,
   said two-way liquid valve having a seal member, said seal member being movably positioned within said open tip end, between an closed position with said seal member engaging the interior surface of said body member proximate said first open tip to preclude fluid flow out of said hollow body member first open tip end, and an open position with said seal member disengaging said interior surface of said outlet region to permit flow into or out of said hollow body member,
   the improvements comprising:
      a stem shroud, said stem shroud having a proximal end affixed to said first open tip end and an open distal end;
      an elongated notch, said elongated notch within said stem shroud having an open end proximate said open distal end and a closed end proximate said proximal end,
      an angled stem member, said angled stem member having an interior member and an engagement member, said interior member being affixed to said seal member to extend into said stem shroud and said engagement member angled to extend through said elongated notch;
      whereby when said seal member is in said closed position, said engagement member extends through said notch at said open end and pressure on said engagement member in the direction of said seal member moves said seal member out of contact with said interior wall, thereby placing said liquid valve in an open position and permitting liquid to be discharged axially from said hollow body member, through said stem shroud.

2. The siphoning device of claim 1, wherein said seal member is a ball valve member having a horizontal circular cross-section and an oval vertical cross-section, said ball valve member having a diameter greater than the diameter of said first open tip end.

3. The siphoning device claim 1, wherein said engagement member extends away from said interior member at substantially a right angle.

4. The siphoning device of claim 1, wherein said interior member and said engagement member substantially form an "L" shape.

5. The siphoning device of claim 1, wherein said stem shroud has a "C" shaped cross-section.

6. The siphoning device of claim 1, further comprising an air vent, said air vent being positioned proximate said elongated body second open end, said vent having a cross-sectional area substantially less than said fluid flow opening cross-sectional area.

7. The siphoning device of claim 6, wherein said air vent has a cross-sectional area of less than about 6 mm.

8. The siphoning device of claim 6, wherein said fluid flow opening has a cross-sectional area at least four times that of said air vent.

9. The siphoning device of claim 6, wherein said fluid flow opening has a cross-sectional area on the order of at least about 100 mm.

10. The siphoning device of claim 6, further comprising a vent collar, said vent collar being supported on said hollow body member over and spaced from said air vent.

11. The siphoning device of claim 10, wherein said hollow body further comprises a radially outward extending flange member, said flange member being positioned between said air vent and said elongated body second open end, and said vent collar further comprises a radially inward extending flange region, said vent collar flange region being supported on said hollow body flange member.

12. The siphoning device of claim 11, wherein said vent collar has a first end proximal to said hollow body second open end and a second end distal relative to said hollow body second open end, said flange region extending from said hollow body proximal end.

13. The siphoning device of claim 12, wherein said vent collar distal end has a periphery at least about 1 mm greater than the periphery of said elongated body member.

14. The siphoning device of claim 10, wherein said vent collar distal end has a periphery at least about 2 mm greater than the periphery of said elongated body member.

15. A siphoning device, comprising:
   an elongated hollow body member, said body member having an interior surface and a first open tip end with a fluid flow opening, said fluid flow opening having a cross-sectional dimension, and a second open end,
   a two-way liquid valve, said two-way liquid valve being positioned within said first open tip end, and
   an air pump member, said air pump member interacting with said second end of said body region to expel air from said hollow body member and to draw liquid into said hollow body member,
   said two-way liquid valve having a seal member, said seal member being movably positioned within said open tip end, between an closed position with said seal member engaging the interior surface of said body member proximate said first open tip to preclude fluid flow out of said hollow body member first open tip end, and an open position with said seal member disengaging said interior surface of said outlet region to permit flow into or out of said hollow body member,
   the improvements comprising:
      an air vent, said air vent being positioned proximate said elongated body second open end, said air vent having a cross-sectional area substantially less than said fluid flow opening cross-sectional area, thereby substantially restricting air flow through said air vent into said body member relative to fluid flow through said fluid flow opening into said body member.

16. The siphoning device of claim 15, wherein said air vent has a cross-sectional area of less than about 6 mm.

17. The siphoning device of claim 15, wherein said fluid flow opening has a cross-sectional area at least four times that of said air vent.

18. The siphoning device of claim 15, wherein said fluid flow opening has a cross-sectional area on the order of at least about 100 mm.

19. The siphoning device of claim 15, further comprising a vent collar, said vent collar being supported on said hollow body member over and spaced from said air vent, whereby air flow into said body member, through said air vent, is not prevented.

20. The siphoning device of claim 19, wherein said hollow body further comprises a radially outward extending flange member, said flange member being positioned between said air vent and said elongated body second open end, and said vent collar further comprises a radially inward extending flange region, said vent collar flange region being supported on said hollow body flange member.

21. The siphoning device of claim 20, wherein said vent collar has a first end proximal to said hollow body second open end and a second end distal relative to said hollow body second open end, said flange region extending from said hollow body proximal end.

22. The siphoning device of claim 21, wherein said vent collar distal end has a periphery at least about 1 mm greater than the periphery of said elongated body member.

23. The siphoning device of claim 20, wherein said vent collar distal end has a periphery least about 2 mm greater than the periphery of said elongated body member.

24. A siphoning device, comprising:
an elongated hollow body member, said body member having an interior surface and a first open tip end with a fluid flow opening, said fluid flow opening having a cross-sectional dimension, and a second open end,
a two-way liquid valve, said two-way liquid valve being positioned within said first open tip end, and
an air pump member, said air pump member interacting with said second end of said body region to expel air from said hollow body member and to draw liquid into said hollow body member,
said two-way liquid valve having a seal member, said seal member being movably positioned within said open tip end, between an closed position with said seal member engaging the interior surface of said body member proximate said first open tip to preclude fluid flow out of said hollow body member first open tip end, and an open position with said seal member disengaging said interior surface of said outlet region to permit flow into or out of said hollow body member,
the improvements comprising:
a stem shroud, said stem shroud having a C-shaped cross-section with a proximal end affixed to said first open tip end and an open distal end;
an elongated notch, said elongated notch within said stem shroud having an open end proximate said open distal end and a closed end proximate said proximal end,
an angled stem member, said angled stem member having an interior member and an engagement member, said interior member being affixed to said seal member to extend into said stem shroud and said engagement member angled at substantially a right angle to extend through said elongated notch;
an air vent, said air vent being positioned proximate said elongated body second open end, said vent having a cross-sectional area substantially less than said fluid flow opening cross-sectional area;
a radially outward extending flange member, said flange member being positioned between said air vent and said elongated body second open end,
a vent collar, said vent collar having a first end proximal to said hollow body second open end and a second end distal relative to said hollow body second open end, and a radially inward extending flange region, flange region extending from said hollow body proximal end and being supported on said hollow body flange member over and spaced from said air vent,
whereby when said seal member is in said closed position, said engagement member extends through said notch at said open end blocking fluid flow; when said air pump member is compressed, and said seal member is in said closed position, air from said air pump member is expelled through said air vent; when pressure is released from said air pump member said seal member moves to said open position and fluid is brought into said body member, said fluid entering said greater cross-sectional area of said fluid flow opening cross-sectional area with less resistance that said ai vent; and when pressure is placed on said engagement member in the direction of said second open end, said seal member out of contact with said interior wall, thereby placing said liquid valve in an open position and permitting liquid to be discharged axially from said hollow body member, through said first open tip end fluid flow opening and along said stem member.

25. The siphoning device of claim 24, wherein said air vent has a cross-sectional area of less than about 6 mm.

26. The siphoning device of claim 24, wherein said fluid flow opening has a cross-sectional area at least four times that of said air vent.

27. The siphoning device of claim 24, wherein said fluid flow opening has a cross-sectional area on the order of at least about 100 mm.

28. The siphoning device of claim 24, wherein said vent collar distal end has a periphery at least about 1 mm greater than the periphery of said elongated body member.

29. The siphoning device of claim 24, wherein said vent collar distal end has a periphery at least about 2 mm greater than the periphery of said elongated body member.

30. The method of liquid transfer using a device having an elongated hollow body member having an interior surface and a first open tip end with a fluid flow opening having a cross-sectional dimension, and a second open end, a two-way liquid valve being positioned within said first open tip end, and an air pump member interacting with said second end of said body region to expel air from said hollow body member and to draw liquid into said hollow body member,
said two-way liquid valve having a seal member movably positioned within said open tip end, between an closed position with said seal member engaging the interior surface of said body member proximate said first open tip to preclude fluid flow out of said hollow body member first open tip end, and an open position with said seal member disengaging said interior surface of said outlet region to permit flow into or out of said hollow body member,
comprising the steps of:
enabling said two way liquid valve to fall to the closed position;
constricting said air pump member to pump air out of an air vent hole and form a vacuum within said body member;

inserting said first open tip end into a liquid such that the stem shroud and elongated notch within said stem shroud are below the surface of said liquid,
releasing said air pump member;
moving said two way liquid valve to said open position through pressure from said vacuum;
siphoning liquid into said device through said two way liquid valve, air being substantially prevented from entering said hollow body member by said air vent small cross-sectional area,
protecting a user from inadvertent contact with liquid that flows out of said air vent hole with a vent collar,
withdrawing said outlet region from said liquid,
enabling said two way liquid valve to fall to the closed position to restrict flow of said liquid out of said device,
moving said device to a desired location,
placing the engagement member of an angled stem member adjacent a surface to move said two way liquid valve into said open position
dispensing at least a portion said liquid from said body member to said desired location
wherein a said liquid valve preventing the flow of liquid from said device while permitting fluid flow into said device.

31. The method of claim 30 further comprising the step of repeatedly constricting and releasing said air pump member thereby drawing additional liquid into said device prior to dispensing said liquid in said desired location, said air vent enabling repeated constricting of said air pump by providing an outlet to said air other than said open tip end.

32. The method of claim 30 further comprising the step of separating multiple layers of immiscible liquids by submersing said stem shroud into a first of said multiple layers and siphoning only said first of said multiple layers into said device.

* * * * *